(12) United States Patent
Neijzen et al.

(10) Patent No.: US 12,339,233 B2
(45) Date of Patent: Jun. 24, 2025

(54) OPTICAL DETECTION OF A SUBSTANCE IN FLUID

(71) Applicant: SIEMENS HEALTHINEERS NEDERLAND B.V., The Hague (NL)

(72) Inventors: Jacobus Hermanus Maria Neijzen, Heeze (NL); Jeroen Hans Nieuwenhuis, Waalre (NL); Arie Rombertus Van Doorn, Zaltbommel (NL); Matthias Irmscher, Eindhoven (NL)

(73) Assignee: Siemens Healthineers Nederland B.V., The Hague (NL)

( * ) Notice: Subject to any disclaimer, the term of this patent is extended or adjusted under 35 U.S.C. 154(b) by 430 days.

(21) Appl. No.: 16/065,458

(22) PCT Filed: Dec. 20, 2016

(86) PCT No.: PCT/EP2016/081819
§ 371 (c)(1),
(2) Date: Jun. 22, 2018

(87) PCT Pub. No.: WO2017/108726
PCT Pub. Date: Jun. 29, 2017

(65) Prior Publication Data
US 2019/0025210 A1 Jan. 24, 2019

(30) Foreign Application Priority Data
Dec. 24, 2015 (EP) ..................................... 15202672

(51) Int. Cl.
*G01N 21/64* (2006.01)
*G01N 21/552* (2014.01)
(Continued)

(52) U.S. Cl.
CPC ......... *G01N 21/648* (2013.01); *G01N 21/552* (2013.01); *G01N 21/76* (2013.01); *G01N 33/54326* (2013.01); *G01N 33/54373* (2013.01)

(58) Field of Classification Search
CPC ........... G01N 21/648; G01N 33/54373; G01N 21/552; G01N 33/54326; G01N 21/76
See application file for complete search history.

(56) References Cited

U.S. PATENT DOCUMENTS

| 6,277,627 B1 * | 8/2001 | Hellinga | ............. | G01N 33/582 |
| | | | | 204/400 |
| 9,822,399 B2 | 11/2017 | Saito et al. | | |

(Continued)

FOREIGN PATENT DOCUMENTS

| EP | 2664914 A1 * | 11/2013 | ............... C07H 1/06 |
| EP | 2873976 A1 | 5/2015 | |

(Continued)

OTHER PUBLICATIONS

"UCSB ScienceLine." http://scienceline.ucsb.edu/getkey.php?key=5276 (Year: 2016) Retrieved Mar. 29, 2024.*

(Continued)

*Primary Examiner* — Dennis White
(74) *Attorney, Agent, or Firm* — Dugan & Dugan, PC

(57) ABSTRACT

The invention relates to a system (1) for optically detecting at least one substance in a fluid (200). The system (1) comprises particles (400, 410) arranged to be dispersed in the fluid (200), each one comprising a magnetic bead (400) and an agent (410). The agent (410) is reactive with said substance such that it gives a specific optical response upon a determined optical excitation or a chemical reaction. The system (1) further comprises a chamber (330) to contain said fluid (200) and particles (400, 410). The chamber (330) is closed at one side by a window (310) optically transparent (Continued)

to the wavelengths of said optical response and said optical excitation. The system (1) further comprises an optical reading system (100) adapted to detect at least a portion of said optical response. The system (1) further comprises magnetic sources (103) arranged to magnetically move the particles (400, 410) onto or close to the window (310). The optical reading system (100) is positioned to receive at least a portion of the optical response from the at least one agent (410) located onto or close to the window (310). The invention relates further to a disposable and a method.

28 Claims, 2 Drawing Sheets

(51) Int. Cl.
*G01N 21/76* (2006.01)
*G01N 33/543* (2006.01)

(56) References Cited

U.S. PATENT DOCUMENTS

| | | |
|---|---|---|
| 2006/0257958 A1 | 11/2006 | Bruno |
| 2009/0246796 A1 | 10/2009 | Bernard |
| 2009/0253181 A1 | 10/2009 | Vangbo |
| 2009/0321662 A1* | 12/2009 | Ohtsuka ............ G01N 33/54333 250/459.1 |
| 2010/0092996 A1* | 4/2010 | Verschuren .......... G01N 21/553 435/7.1 |
| 2010/0330698 A1 | 12/2010 | Evers |
| 2011/0027916 A1 | 2/2011 | Nieuwenhuis |
| 2011/0065086 A1 | 3/2011 | Bruno |
| 2011/0168918 A1 | 7/2011 | Wimberger-Friedl |
| 2011/0262893 A1 | 10/2011 | Dryga |
| 2013/0109030 A1 | 5/2013 | Hardeman |
| 2014/0057366 A1 | 2/2014 | Dittmer |
| 2014/0134602 A1* | 5/2014 | Van Zon ............... G01N 21/648 435/7.1 |
| 2014/0234865 A1* | 8/2014 | Gabriel .............. G01N 33/5026 435/7.21 |

FOREIGN PATENT DOCUMENTS

| | | |
|---|---|---|
| TW | I347438 B | 8/2011 |
| WO | 20141133614 A1 | 7/2014 |

OTHER PUBLICATIONS

Held, P. "The importance of using the appropriate microplate for absorbance measurements in the ultraviolet region of the spectrum." Winooski, Vermont (2009). (Year: 2009).*

Tian, Yaji et al "Structure-based Design of Robust Glucose Biosensors using a Thermotoga Maritima Periplasmic Glucose-Binding Protein" Cold Spring Harbor Laboratory Press, 2008.

Molecular Probes Handbook, Chapters 19 and 21, 2010.

* cited by examiner

OPTICAL DETECTION OF A SUBSTANCE IN FLUID

CROSS-REFERENCE TO PRIOR APPLICATIONS

This application is the U.S. National Phase application under 35 U.S.C. § 371 of International Application No. PCT/EP2016/081819, filed on Dec. 20, 2016, which claims the benefit of European Patent Application No. 15202672.0, filed on Dec. 24, 2015. These applications are hereby incorporated by reference herein.

FIELD OF THE INVENTION

The invention relates to sensing systems and methods allowing optical detection of substances in fluids, in particular in biological fluids (e.g. blood, serum, plasma, saliva, urine), via the use of agents reactive to said substances such that they give specific optical responses upon a determined optical excitation or a chemical reaction. The detection of those substances may be useful for different purposes, such as a measurement of a chemical substance in a fluid and/or healthcare diagnosis in case those substances can be linked to specific disease or other problems. Such types of detections might be particularly useful to identify concentration of small substances in a biological sample.

BACKGROUND OF THE INVENTION

From the various available technologies enabling the detection of particles in a fluid, it is known the use of fluorescent or chemiluminescent agents in a biological sample, which enables the production or the change of a fluorescent or luminescent response as a result of their interactions with some specific substances present in the sample.

The detection of those optical responses gives then an indication of the presence or concentration of those substances (e.g. glucose) in the sample.

The fluorescent or luminescent response is difficult to detect in opaque samples due to absorption and scattering of the emitted wavelengths in the samples.

In order to address this problem, it is known to process the samples, by filtering and/or chemical treatment, to obtain a resulting sample that will be more transparent while still comprising the substances to be detected.

The reliability of the measurements is therefore increased.

SUMMARY OF THE INVENTION

One of the main purpose of the invention is the enhancement of the sensitivity and reliability of the existing assays and/or optical detection systems.

Another purpose of the invention is the possibility to detect some substances in a fluid, even if this fluid is optically opaque.

Another purpose is to meet the two aforementioned purpose with a low-cost system of detection of those substances.

So as to address those problems and purposes, the invention proposes an optical detection system according to claim 1. Optional features of this system can be found in claims 2 through 11.

This invention allows the capture of substances in the bulk of the fluid by dissolving or suspending or diluting or dispersing the agents in the fluid, and therefore involving their interactions with the targeted substances during an incubation time.

The use of magnetic beads, attached to the agents, together with the use of magnetic source, allows a magnetic manipulation of the beads-agent complexes in such a way that they are magnetically moved (attracted or repulsed depending on the magnet polarity) to the window for detection purpose.

Furthermore, this magnetic source allows retaining the magnetic beads-agents onto or close to the window without necessarily using any other retaining means, during the detection.

It is to be noted that the magnetic beads may be directly or indirectly attached to the agents by any means of attachment. For example, the attachment may be made by a chemical bond (e.g. covalent bond), the agent may be a coating applied onto the surface of the magnetic bead or the agent may be indirectly bound or attached to the magnetic bead through an intermediary biomaterials such as for instance the targeted substance.

As a consequence, the optical detection can be performed on one side of the chamber (also called thereafter fluid container), through a transparent window, minimizing the amount of fluid between the agents and the optical system (i.e. the detector and the optional source).

Furthermore, this dragging of the complexes magnetic particles/agents to the window decreases significantly the background optical noise or signals which may exist in the bulk of the fluid.

Sensitivity and reliability is therefore improved.

And the problem of opacity of the fluid is therefore withdrawn.

And the fluid does not need to be pre-processed (filtering and/or chemically treating) for the detection purpose. So the system of the invention reduces significantly the costs of the optical detection. In particular, the design and functionalities of the disposables used in the system of the invention (whose disposables comprises said chamber, agents and beads) can be drastically simplified and their costs drastically reduced.

Sensitivity and speediness of the detection can be improved further by, optionally, configuring further the magnetic sources to generate rotating magnetic fields so as to enhance the mixing of the agents in the fluid, and thus to increase the probability of their interactions with the substances.

The agent of the invention is arranged for interacting or for being reactive, directly or indirectly, with the targeted substance (or analyte). This interaction or reaction may be of chemical and/or physical and/or electrostatic type. This agent is further arranged to provide an optical response, or an optical response change due, directly or indirectly, to this interaction or reaction. Such an agent may be a protein having a reporting element (or reporter) that leads to said change of optical response when interacting with the targeted substance or analyte, known in the art.

Typically, these agents are either photoactivatable upon interaction with the targeted substance, or are sources of photons upon a chemical reaction with the targeted substance or analyte. In the first case said optical response is for example a fluorescent signal or response, a colorimetric signal or response, or a luminescent signal or response activatable by electromagnetic excitation energy. In the second case, those agents may have chemiluminescent properties, which can produce electromagnetic energy or optical response if chemically reacting with the targeted substance.

An example of agents that can be used are ion-selective fluorescent reporter proteins, used in the life sciences, e.g. for intracellular imaging—e.g. 'Molecular Probes Handbook' which gives a good overview and can serve as a reference (specifically, chapters 19 and 21).

Another example of agent the structure of a protein ('an agent') that can bind to analytes (here glucose) and undergoes a change in fluorescence upon binding (U.S. Pat. No. 6,277,627 or "Structure-based design of robust glucose biosensors using a *Thermotoga maritima* periplasmic glucose-binding protein" from Yaji Tian et al., Cold Spring Harbor Laboratory Press, May 30, 2008).

Other kinds of such agents can be found in the literature.

The invention involves also the use of magnetic beads. Such magnetic beads may be comprise typically superparamagnetic such that they can be activated and move by an external magnetic field generated. For example, magnetic beads made by the company Ademtech may be used.

The agent can be coupled to the magnetic bead via for example an EDC cross-linker that activates carboxyl groups for spontaneous reaction with primary amines or a protein, or cysteine residues (all well-known in the art).

Alternatively, the agent can be coated on the surface of the magnetic bead.

Alternatively, the agent(s) may be initially provided in the system and in the fluid separately from the magnetic beads (i.e. not attached one to the other), and they bind one to the other only via the analyte (or targeted substance) or another intermediary component or substance. The final complex comprises the agent, the magnetic bead and the analyte (or intermediary component), the latter being sandwiched between the magnetic bead and the agent. In this alternative embodiment, the agent can still interact with the analyte (or intermediary component) at an interaction site of the analyte (like in the two previous alternative embodiments, to produce an optical response if excited) and the magnetic bead is provided with a biomaterial (e.g. protein, antibody, nucleic acid) that specifically binds to a binding site of the analyte (or the intermediary component). This embodiment can be particularly useful if it is desirable to put into contact first the magnetic beads and the analytes, and second the analytes (bonded with magnetic beads) with the agents. Or reversely: putting into contact first the agents and the analytes, and second the analytes (bonded to the agents) with the magnetic beads. For example the two steps may be separated by some appropriate fluid processing or fluid guiding between the two steps. The two steps may be implemented in two respective different chambers of a platform. This may be particularly interesting in molecular diagnostics applications where fluid processing necessitates typically several steps.

In the next sections of this document, "particle" shall mean an assembly of a magnetic bead with an agent, directly or indirectly attached one to the other. "Indirect" combination can include the aforementioned case of an analyte, or any other intermediary component, sandwiched between the agent and the magnetic bead.

It is to be noted that the initial surface of a particle is or is not provided with any other biomaterial such as antibody or nucleic acid segment (provided with epitopes or sequences that specifically bind to some analytes (e.g. a protein, a nucleic acid, small molecules—i.e. with a weight smaller than 1000 Dalton, peptides, ions) of the fluid.

The surface defined by the interface between the window and the fluid container (also called thereafter "sensor surface") may be preferably not functionalized with specific bonds to a target analyte or to an analogue of the target analyte in the fluid. This particular embodiment, together with the functionalization of the particles may lead to a sandwich or a competitive assay between the particle and the sensor surface, well-known in the art, which is not the primary purpose of this invention. It is to be noted that only the magnetic source allows the particles to be retained onto or close to this interface and there is no need of additional means to retain the particles in the fluid container onto or close to the interface with the window.

The system of the invention will not require therefore any preparation of the sensor surface with biomaterials, which therefore will reduce further some costs of manufacturing this sensor surface, especially the costs of the disposable to be used in the system.

The optical source which may be used to potentially excite the agents can be any type of electromagnetic source, such as for example a LED or a laser source.

The optical detector may be for example a photomultiplier tube (PMT), a photospectrometric detector, a camera (e.g. a 2D or 3D camera, e.g. a CMOS camera, a CCD camera), a multispectral camera and/or a photodiode.

For instance, a PMT or a multispectral camera may be appropriate to detect fluorescence or luminescence and a photospectrometric detector may be appropriate to detect colorimetry.

In a specific embodiment of the invention, the optical system comprises a Totally Internal Reflector ("TIR") system. In particular:

the refractive index of the window material is higher than the refractive index of the fluid to be provided, defining accordingly an optical critical angle from the normal of the interface between the window and the fluid container such that an electromagnetic wave propagating in the window and incident to this interface at an angle greater than the critical optical angle is totally reflected onto this interface, the optical source is positioned such that the total reflection occurs on this interface.

An effect of TIR is the creation in the fluid of an evanescent wave of typically a few tenths to a few hundred of nanometers thickness over the interface between the fluid and the portion of the window which is receiving the incident optical wave. This evanescent wave illuminates or excites the particles which gives a specific optical response (as aforementioned) if they have been interacted or are interacting with the targeted analyte. This optical response may be linked to an increase of the scattered intensity in comparison with the case of it would have not interacted with the substance. This optical response may be linked to the emission of determined wavelengths specific to its optical signature (e.g. fluorescence). This optical response may be linked to the absorption of determined wavelengths specific to its optical signature (e.g. color). It is to be noted that the magnetic bead (attached to agent) may further scatter and/or absorb if it is present in the evanescent wave too, bringing a further information on the presence of the particle on or close to the window, which may have to be taken into account in the data retrieving process.

This photo-scattering and/or photo-absorption and/or photo-emission can be directly or indirectly detected by said detector.

For instance a spectrometric detector, a camera (e.g. CCD or CMOS camera), a photodiode and/or a microscope may be positioned above the window to detect directly the peak intensity(ies) at the emission wavelength(s) and/or scattering wavelength(s) and/or the lack of intensity at the absorbed wavelength(s). Such direct detection has the advantage to offer large numerical aperture, with potential other optics for optimization purpose or the detection.

Alternatively the frustration of the light reflected onto the sensor surface, due to the presence of the particles into the evanescent field, around the scattered and/or absorbed and/or emitted wavelength(s), can also be detected by an adapted detector positioned to receive such reflected light, such FTIR detector being also used in the frame of the invention. Such detected Frustrated Totally Internal Reflection ("FTIR") signal comprises a lower intensity in the received signal which is due to presence of particles in the evanescent wave. It is to be noted that such a FTIR system may be seen as a particularly non-cumbersome system since it is positioned on only one side of the window and with a typical tilted angle particularly beneficial for an integration in the housing of a detecting device—which may be also called a "reader" or "analyzer". Moreover the magnetic source of the invention can be positioned in between the source and the detector of the FTIR system, enhancing the integration capacity in a handheld device.

In another embodiment these two types of detection can be used together, to enhance sensitivity, reliability and robustness of the detection. The two detectors can also be complementary. For example the first detector can detect the fluorescence or luminescence emitted by agents activatable from the interaction with an analyte, while the second detector detects the light scattering of the magnetic beads in the evanescent field.

In a specific embodiment, the agents are chemiluminescent, and the photons emitted by the agents can be directly detected by an optical detector, without necessarily using optical source. For instance a spectrometric detector, a camera (e.g. CCD or CMOS camera), a photodiode and/or a microscope may be positioned above the window to detect directly the peak intensity(ies) at the emission wavelength(s) from the chemiluminescent agents. Such direct detection has the advantage to offer large numerical aperture, with potential other optics for optimization purpose. As aforementioned for non-chemiluminescent agents, magnetically positioning those chemiluminescent agents close to the window can clearly enhance the sensitivity and robustness of the system, since the fluid will not interfere so much, and any other optical background or signal in the bulk of the fluid may be easily withdrawn.

The detector(s) of the invention may be further optimized to better identify, in the detected light, the optical response(s) of the agent(s) to be detected. For example, the detector may have been configured or tuned to exhibit a higher resolution around the wavelength(s) of the expected optical response(s). In a particular embodiment, the detecting system of the invention has a prior knowledge of the optical response value(s) (frequency(ies) or wavelength(s)) of the agent(s) once excited or illuminated or chemically reacted with the targeted analyte, stored in its memory, which may be used to help for identifying the optical response(s) in the detected signal.

In an optional embodiment of this optical system, the detecting system is arranged to perform a spectral analysis of the detected wave. This may be very useful to detect fluorescence, luminescence and/or color response in the waves received by the optical detector.

This detection system may comprise in particular a processor (or processing means), of hardware and/or software type positioned downstream the detector per se to process and analyze the data received by the detector, which is adapted to retrieve from the detected spectrum presence of said at least one particle. The identification in the detected signals of the optical response from the activated agents allows in particular the determination of the concentration or counting of the particles present on or close to the window, especially by identifying the intensity(ies) of the optical response(s). For instance, if the intensity of an activated agent is found three times (absolute value) higher than the intensity that one can expect from a single particle, one can deduce that three particles have been detected.

The step of retrieving the optical responses of the particles due to interaction with targeted analytes, from the data received at the detector, may be performed by identifying in a spectrum the wavelength(s) corresponding to peak(s) (or trough(s)) in the received intensities. This identification can be done also on the basis of the knowledge of the agent used in the system (which has some determined optical signatures associated with it). This identification can be done on an absolute basis or on a relative-basis. In the second case, the processor may subtract a background from the received signal. Alternatively or additionally, the processor may calculate a ratio between the intensity of those peaks (or troughs) and a reference wavelength—the latter being representative of some specific environmental conditions of the measurement. Concentration or counting of particles onto or close to the sensor surface can then be assessed from this ratio. Molecularly, and in the specific case of detecting analytes using agents emitting fluorescent or chemiluminescent photons, this allows the identification of a relative shift of the fluorescent spectrum upon binding of the analytes.

In case the magnetic beads produce an additional response in the detected wave, a combination of both the optical response and the additional response in the detected wave due to presence of particles may improve therefore significantly the sensitivity of the sensing system, since the probability to miss some particles in the detected signal is lower.

The invention may open accordingly to new types of signal analyses based on lower amount of particles to be detected or more opaque fluid, and thus to new applications.

Furthermore, the invention is about the detection of particles arranged to be dissolved (or dispersed, suspended) in the fluid (typically a liquid, e.g. a biological sample: blood, saliva, etc.). It means that the system stores these particles in such a way that, once the fluid is provided into the system (e.g. the biological sample is collected from a patient), the particles can move in the bulk of this fluid and therefore interact with some substances of the fluid. These interactions in the volume of the sample is of course an aspect very interesting of the invention since it may lead to a lot of applications requiring such interactions. As aforementioned this mixing may be further improved by the use of said magnetic sources.

After these particles are sufficiently incubated in the fluid, their presence onto or close to the window is detected. "Close to" means not far enough from the window such that the fluid does not disturb significantly the measurements based on predetermined tolerated optical disturbances. In case an optical technology based on an evanescent wave is used, "close to" means more especially not too far from the window so as to be at least partly comprised in the evanescent wave.

The particles are moved by magnetic fields generated by said magnetic source.

In a particular embodiment, said magnetic source may be positioned between the optical source (if any) and the optical detector, so as to facilitate the integration of the overall system (including circuitry) in the housing of a detecting device while keeping a reasonable size for this optical device, adaptable for a handheld use. Moreover, the overall arrangement of such detecting device may be compact, leading to an assembly more robust with appropriate protection elements provided between the different components of this device. Optionally, the magnetic source may operate in a first mode for the attraction and in a second mode for the repulsion of the particles towards or outwards the window. Furthermore it can be configured (thanks to e.g. a determined protocol) to mix the particles in the bulk of the fluid.

In another optional embodiment, the (internal hollow) chamber or container of the fluid is closed at a second side by a second window optically transparent to the wavelengths of the optical response(s) of the particle(s) and the potential optical excitation(s) of the particle(s). This second window may be for example positioned so as to face the first window. By this way, this fluid container can be used for different purpose, in two different ways. It may be particularly interesting for a rapid detection of analytes, especially due to the self-referencing nature of the measurement.

As examples, the substance (or analyte) targeted by the system and method of the invention may be, without any limitation whatsoever, one of several of these substances, e.g. Albumin, Alkaline Phosphatase, Alanine Aminotransferase, Amylase, Aspartate Aminotransferase, Urea Nitrogen, Calcium, Chloride, Creatinine Phosphokinase, Creatinine, Direct Bilirubin, γ-Gamma-Glutamyl Transpeptidase, Glucose, High-Density Lipoprotein, Lactic Dehydrogenase, Lipase, Potassium, Sodium, Phosphorus, Total Bilirubin, Total Cholesterol, Triglyceride, Total Protein, Uric Acid, total carbon dioxide (TCO2), Anion Gap, antibody, protein, nucleic acid, molecules relative weight smaller than 1000 Dalton.

As an option, the invention is further arranged such that said at least one particle (i.e. agent+magnetic bead) is stored in a dried assay before the fluid is provided to the system. This storage may be localized inside or outside the fluid container. The storage of the particles in a dried assay allows the platform to be stored, sold with the embedded particles, ready to use.

As an alternative or combined option, these particles may be stored in an assay zone of a disposable, such disposable further comprising said fluid container. The disposable may further comprise a fluidic path with an external inlet, and passing through said assay zone and the fluid container. This fluid path may be a microfluidic path, with active and/or passive pumping or suction or capillary suction to drive the flow of the fluid, with microelements (e.g. valves, stops, etc.) to process the fluid in different steps of processing.

As a further option to the invention, the window material may be arranged to be transparent to a narrow-band of the incident wave emitted by the optical source, around said at least one optical response(s). Alternatively or in combination, the detector and/or the processor may be provided with narrow-band filter(s) around said at least one optical response(s). This embodiment allows the system to retain only a portion of the detected signal around the optical response. It can be particularly interesting for improving the signal-to-noise ratio of the optical response from the remaining part of the optically detected signal. It can be used also to focus only on the optical response(s) while filtering out any unwilling information outside this optical response(s).

The system may further comprise one or several other agents of a second type (in comparison of said "at least one particle" of claim 1), arranged to be dissolved or suspended in the fluid too, chemically reactive with a substance of another type such that it gives a specific second optical response, different from the first optical response of the agent of the first type, upon a determined second optical excitation. This difference of optical responses between these two types of agents may be due to the use of different material used for the agents which have different optical properties when reacting with the corresponding substances, and so generating different optical responses. Optionally, the agent of the second type is attached to a magnetic bead too. This option is particularly interesting for a system multiplexing different kinds of substances. This embodiment may be implemented from the same initial waves or from different incident waves emitted separately over time.

The invention further relates to a disposable according to any of claims 12 to 14 and the Method of claim 15 or 16.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE INVENTION

Figure 1:
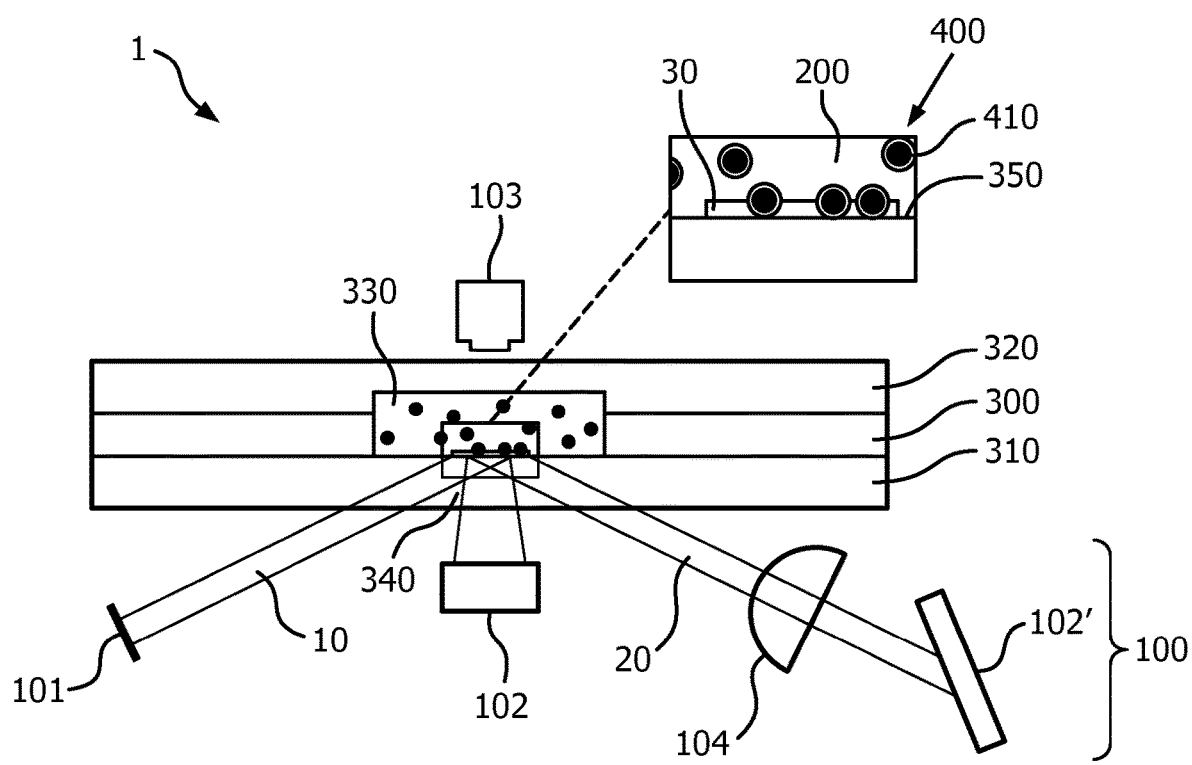
FIG. 1 shows a schematic side-view of an optical system.
Figure 2:
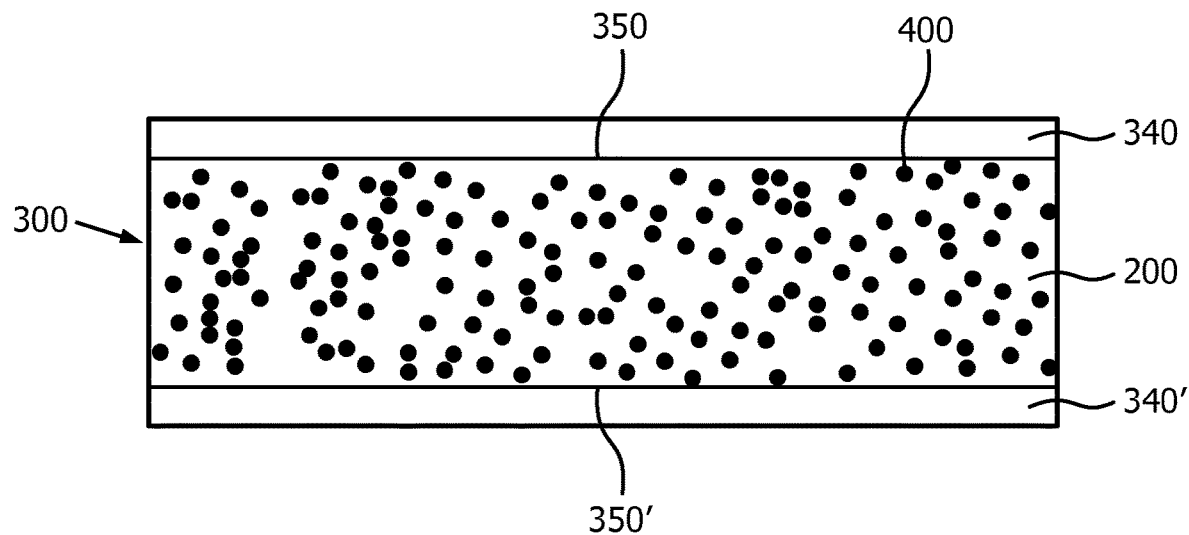
FIG. 2 shows a schematic side view of the fluid container before detection.
Figure 3:
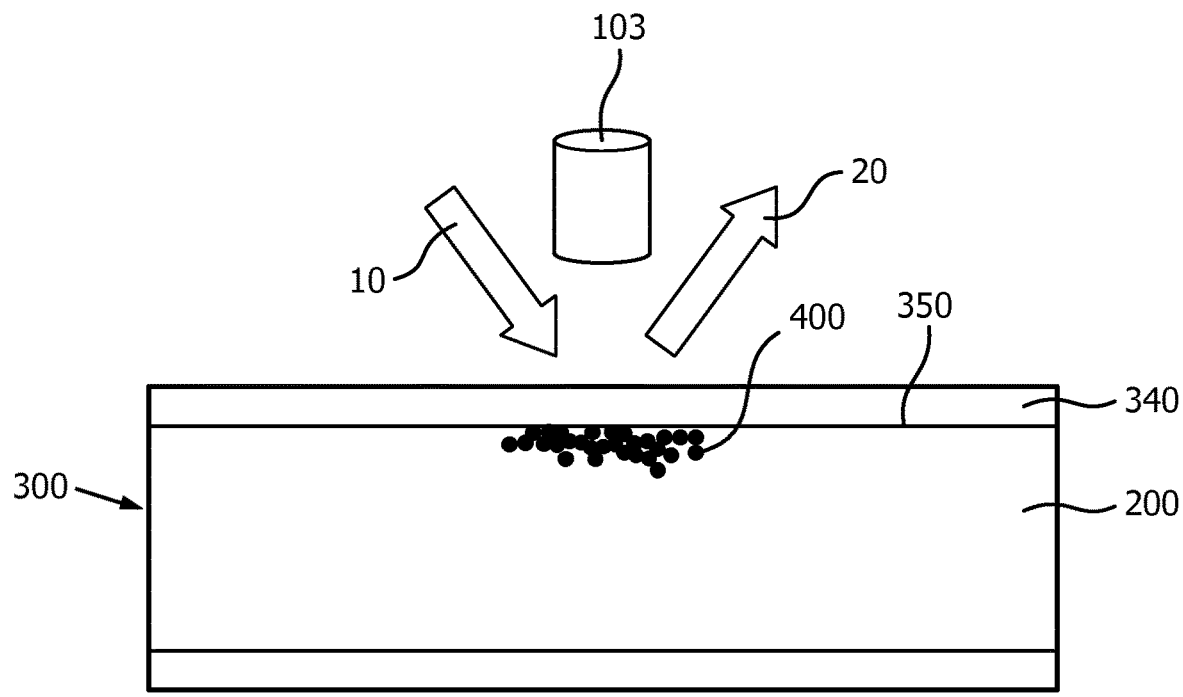
FIG. 3 shows a schematic side view of the fluid container during detection.

FIG. 1 shows a schematic view of a TIR system 1, comprising a reading system 100 and a platform 300. The platform 300 embeds particles 400 and has a sensor surface 350 extending between a transparent window 340 and a fluid container 330. The platform 300 and the reading system 100 are arranged to closely operate one to the other such that the reading system 100 can emit light (and/or other electromagnetic wave) to and receive light (and/or other electromagnetic wave) from the sensor surface 350 of the platform 300.

In particular, the reading system 100 comprises:

a light emitter 101, e.g. at least one light emitting diode (LED) or a laser, to emit a light beam or wave 10 onto the platform 300;

an arrangement (not referenced in FIG. 1) to receive a sensor platform 300, such that the sensor surface 350 can receive the light emitted from the light emitter 101;

a light detector 102, e.g. a 2D camera, e.g. a CMOS or CCD camera, a microscope positioned to detect the some photons from the particles 400 illuminated onto or close to the sensor window 350. Alternatively or in combination, the light detector can comprise a FTIR detector 102' which receives at least a portion of the reflected light 20, which has been reflected by the platform 300. Any optics allowing an optimization of the detection system can be used, such as for example a lens or a prism 104 or any other appropriate optical elements known by the person skill in the art; generally speaking, the light emitter 101, said arrangement and the light detector 102 are configured and positioned one to the others such that a light 10 emitted by the light emitter 101 can be received by the sensor platform 300 positioned in the arrangement, and a light coming from the illuminated sensor surface 350 is received by the light detector 102 or 102'; Optionally, this light detector 102' and/or 102 and/or the optics 104 is/are arranged to detect a spectrum including the wavelengths of the expected optical response of the particles 400 close to the sensor surface 350;

a processor (not shown) positioned downstream the detector 102 and/or 102' and arranged to determine a presence of said particles 400 based on information retrieved from the received light and related to a frustration of the totally internal reflected wave due to presence of particles 400, this retrieved information including some optical response(s) of particles 400 present onto or close to the sensor surface 350; the processor is advantageously arranged to determine and analyze at least a part of the spectrum of the detected light; the processor may be provided in a single housing of the reader 100 (not shown), together with the light emitter 101, the light detector 102 or 102' and the magnetic source 103-103' (described thereafter), and/or in a docking station or local computer (not shown) in a proximate communication with the reader and/or in a remote location in communication with the reader 100 via a communication network.

magnetic source(s) 103 to generate a magnetic field or strength in the fluid 200 to exert forces on the dissolved or suspended particles 400 and whose control allows the manipulation of the particles 400 inside the fluid 200, towards the sensor surface 350 and/or outwards the sensor surface 350 and/or over more complexed motions. This magnetic source 103 may be arranged in horseshoe arrangement, as known in the art.

The platform 300 may be a disposable, optionally mostly made of a polymer material or of any kind of material subject to the optical properties needed for implementing the invention.

In the specific embodiment of FIG. 1, the platform 300 comprises:
  a base part 310 provided with a window material transparent to at least certain wavelengths of the incident light 10, extending from and below the sensor surface 350;
  a cover 320, e.g. a laminate foil, positioned on the base part 310.

The base part 310 and/or the cover 320 may be configured to define microfluidic components between them, such as a detection chamber 330, micrometric channels, other chambers, etc. to process the fluid 200 downstream and upstream the detection chamber 330 (not shown). A surface portion of the base part 310 and/or cover 320 may be used and configured to store some particles 400 in a dried state, preferably upstream or in the detection chamber 330, before the fluid 200 is provided for the detection purpose.

The refractive index of the material of the window 340 is higher than the refractive index of the fluid 200 so as to define an optical critical angle from the normal of the sensor surface 350 such that an electromagnetic wave 10 propagating in this platform material and incident to the sensor surface 350 at an angle greater than the critical optical angle θc is totally reflected onto the sensor surface 350. As well-known, the consequence of this total reflection is the creation of an evanescent wave 30, typically from a tenth to a few hundred nanometers height on the sensor surface 350.

The light emitter 101, the light detector 102 and the platform 300 are configured and positioned one to the others such that, indeed, the incident light 10 is totally reflected onto the sensor surface 350 and the some light 20 coming from the sensor surface is received by the light detector 102 and/or 102'.

The particles 400 may be stored in a dried state, as above-mentioned, and are arranged to be dissolved (or suspended or diluted) in the fluid 200 (typically a liquid, e.g. a biological sample: blood, saliva, etc.). Once the fluid 200 is provided to the system 1 (e.g. the biological sample is taken from a patient), the particles 400 can move in the bulk of this fluid 200 and therefore interact with some substances of the fluid 200. The particles 400 comprise a magnetic material, i.e. a material having such magnetic properties that they can be manipulated and moved to the sensor surface 350 by the action of the magnetic source 103. This magnetic material can be for example superparamagnetic. This magnetic material forms a bead. These particles 400 further comprise an agent 410, bonded to the bead or coated onto the bead (as depicted in FIG. 1). In the case of a coating, this agent material can be provided as a continuous layer 410 on the surface of the particles 400. The agent is chemically reactive with specific substances which may be found in the fluid 200, such that it gives a specific optical response upon a determined optical excitation 10. The size of the particle 400 and the thickness of the layer 410 for the considered agent layer 410 (if the agent is coated onto the magnetic bead) may influence the intensity of this optical response.

It is to be noted that the surface of the particles 400 may not be provided with any other biomaterials (than possibly the agents 410) such as antibodies or nucleic acids (provided with epitopes or sequences that specifically bind to some analytes (e.g., a protein, a nucleic acid) of the fluid 200). Similarly, the sensor surface 350 is preferably not functionalized with specific bonds to a target analyte or to an analogue of the target analyte in the fluid. This particular embodiment, together with the functionalization of the particles 400 may lead to a sandwich or a competitive assay, well-known in the art, which is not targeted in this invention. It is to be noted that only the magnetic source 103 allows the particles 400 to be retained onto or close to the sensor surface 350.

The material of the window 340 may be arranged to be transparent to only a narrow-band of the spectrum of the incident wave 10, around the expected wavelength(s) of said optical response of the particles 400. For example, the window 340 may be made of a material leaving only the blue light going through it knowing that the wavelength of the optical response (scattering and/or absorption and/or emission) of the particles 400 is in the blue spectrum, which would give then mostly a bright response in a detector 102 and a dark response in a FTIR received signal 20 in the FTIR detector 102'. This embodiment may be interesting for filtering out some unwanted wavelengths or discarding the optical response of other types of particles 400, or particles which have not been in contact with the targeted substances (for example some particles 400 of the other types have an optical response in the red spectrum).

Alternatively or in combination, the detector 102 and/or 102' and/or the processor may be provided with a narrow-band filter around the expected optical response(s) of particles 400. This embodiment(s) allows the system 1 to retain only a portion of the received signal 20 around the wavelength corresponding to the optical response. This embodiment can be interesting to improve the signal-to-noise ratio of the targeted optical response from the remaining part of the received signal. It can be used also to focus only on the specific optical response phenomena while filtering out any unwilling information outside the localized resonance.

As already indicated, the system may comprise particles 400 with agents of different types, each type enabling a proper optical response, i.e. having a proper optical response wavelength(s) once their respective agents are excited. This option is particularly interesting for a system multiplexing different kinds of particles. Particularly, if each types of substances to be detected in the fluid 200 corresponds to one specific said type of agent: by this way, the different types of substances may be clearly identified and detected thanks to the invention, by detecting in the received signal the different corresponding optical response(s) in the spectrum and measuring their respective intensities. This embodiment may be implemented from the same initial waves 10 or from different incident waves 10 emitted separately over time.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. For instance, the system of the invention can be used not only with the particles according to the invention, but being used with other types of particles in combination with the particles of the invention. Furthermore it is to be noticed that the invention may use chemiluminescent particles, and the system or method of the invention will not necessarily be used or include optical source.

The invention claimed is:

1. A system for optically detecting at least one substance in a fluid, comprising:
    at least one first agent, wherein:
        the at least one first agent is reactive with the at least one substance, and
        an optical response is produced during interaction of the at least one first agent and the at least one substance;
    a chamber to contain the fluid, wherein:
        the chamber is closed at one side by a window, and
        the window is comprised of a material optically transparent to only a selected portion of a spectrum of incident wavelengths that includes a wavelength of the optical response, the selected portion including visible light wavelengths of only a single color spectrum;
    first and second optical detectors, wherein the first and second optical detectors are arranged and adapted to each detect at least a portion of the optical response, the first optical detector vertically aligned with the window, and the second optical detector positioned differently than the first optical detector on one side of the window;
    a first magnetic bead attached to the at least one first agent to form a particle, the particle stored in a dried assay prior to the fluid being provided to the chamber;
    at least one magnetic source, wherein:
        the at least one magnetic source is arranged to operate in a first mode and a second mode, the first mode for attraction of the first magnetic bead toward the window, and the second mode for repulsion of the first magnetic bead away from the window, and
        only the at least one magnetic source allows the particle to be retained onto or close to a sensor surface extending between the window and the chamber; and
    a processor circuit, wherein:
        the processor circuit determines a quantity of the at least one substance in the fluid based on signals provided by the first and second optical detectors, and
        the first and second optical detectors are each positioned to receive at least a portion of the optical response from the at least one first agent located upon or close to the window.

2. The system of claim 1, wherein the optical response is selected from the group consisting of a fluorescent signal, a colorimetric signal and a luminescent signal upon optical excitation.

3. The system of claim 2, further comprising
    an optical source of an electromagnetic wave,
        wherein a spectrum of the electromagnetic wave comprises the electromagnetic wavelengths of the optical excitation,
        wherein the optical source and an interface between the window and the chamber is a TIR (Totally Internal Reflector) system such that the total reflection of the incident electromagnetic wave emitted from the optical source occurs on the interface, and such that an evanescent optical field is formed accordingly in the fluid on the interface.

4. The system of claim 1, wherein the optical response is a chemo luminescence response to a chemical reaction.

5. The system of claim 4, wherein the first or second optical detector comprises a photomultiplier tube, a spectrometric detector, a camera, a photodiode, or a FTIR (Frustrated Totally Internal Reflection) detector.

6. The system of claim 5, wherein the first or second optical detector is arranged to perform a spectral analysis of a detected electromagnetic wave.

7. The system of claim 6, wherein the at least one substance to be detected comprises one or several of these substances: Albumin, Alkaline Phosphatase, Alanine Aminotransferase, Amylase, Aspartate Aminotransferase, Urea Nitrogen, Calcium, Chloride, Creatinine Phosphokinase, Creatinine, Direct Bilirubin, y-Gamma-Glutamyl Transpeptidase, Glucose, High-Density Lipoprotein, Lactic Dehydrogenase, Lipase, Potassium, Sodium, Phosphorus, Total Bilirubin, Total Cholesterol, Triglyceride, Total Protein, Uric Acid, total carbon dioxide (TCO2), Anion Gap, antibody, protein, nucleic acid, molecules relative weight smaller than 1000 Dalton.

8. The system of claim 1, further comprising
    at least one second agent,
        wherein the at least one second agent is arranged to be dispersed in the fluid,
        wherein the at least one second agent is reactive with at least one other substance such that it gives a second optical response, upon a determined second optical excitation or a chemical reaction.

9. The system of claim 8, wherein the at least one second agent is attached to at least one second magnetic bead.

10. The system of claim 1, wherein an interface between the window and the chamber is not specifically arranged to capture the at least one substance or any analogue of the at least one substance.

11. The system of claim 10, further comprising
    a data processor circuit,
        wherein the data processor circuit is arranged to calculate a ratio between an intensity of the optical response at the wavelength of the optical response and an intensity of an optical response at a reference wavelength in the detected spectrum,
        wherein the data processor circuit is arranged to use the result of this calculation to determine the concentration of the at least one substance.

12. The system of claim 1, wherein the at least one first agent is selected from the group consisting of ion-selective fluorescent reporter proteins and a protein that undergoes a change in fluorescence upon binding with an analyte.

13. The system of claim 1, wherein the at least one magnetic source is further arranged to mix the first magnetic bead in the fluid.

14. The system of claim 1, wherein the first optical detector detects fluorescence or luminescence emitted by the at least one first agent activatable from interaction with the at least one substance, and the second optical detector detects light scattering of the first magnetic bead in an evanescent field.

15. The system of claim 1, wherein the window is comprised of a material optically transparent to only a spectrum of blue light.

16. A method of optically detecting at least one substance in a fluid, comprising:
storing at least one particle comprising a magnetic bead and a first agent in a dried assay,
wherein the first agent is reactive with the at least one substance, and
wherein an optical response is produced during interaction of the first agent and the at least one substance;
providing a chamber with a window,
wherein the window is comprised of a material optically transparent to only a selected portion of a spectrum of incident wavelengths that includes a wavelength of the optical response and a wavelength of an optical excitation, the portion including visible light wavelengths of only a single color spectrum;
providing the at least one particle and the fluid in the chamber;
providing first and second optical detectors, wherein the first and second optical detectors are arranged and adapted to each detect at least a portion of the optical response, the first optical detector vertically aligned with the window, and the second optical detector positioned differently than the first optical detector on one side of the window;
providing at least one magnetic source having a first mode of operation and a second mode of operation, the first mode for attraction of the magnetic bead toward the window, and the second mode for repulsion of the magnetic bead away from the window;
magnetically moving the at least one particle onto or close to the window; and
magnetically retaining the at least one particle onto or close to the window while detecting at least a portion of the optical response from the at least one particle;
wherein only the at least one magnetic source allows the at least one particle to be retained onto or close to the window.

17. The method of claim 16, further comprising
emitting an electromagnetic wave to the window,
wherein the electromagnetic wave comprises the wavelength of the optical excitation such that the wavelength of the optical excitation is totally reflected at an interface between the window and the chamber.

18. The method of claim 16, wherein the optical response is selected from the group consisting of a fluorescent signal, a colorimetric signal and a luminescent signal upon optical excitation.

19. The method of claim 18, further comprising
providing an optical source of an electromagnetic wave,
wherein the spectrum of the electromagnetic wave comprises the wavelength of the optical excitation, and
wherein the optical source and an interface between the window and the chamber is a TIR system,
wherein a total reflection of the incident electromagnetic wave emitted from the optical source occurs on the interface, and
wherein an evanescent optical field is formed accordingly in the fluid on the interface.

20. The method of claim 16, wherein the optical response is a chemo luminescence response to a chemical reaction.

21. The method of claim 20, wherein the first or second optical detector comprises a photomultiplier tube, a spectrometric detector, a camera, a photodiode, or a FTIR detector.

22. The method of claim 21, further comprising performing a spectral analysis of signals provided by the first or second optical detector.

23. The method of claim 22, wherein the at least one substance to be detected comprises one or several of these substances: Albumin, Alkaline Phosphatase, Alanine Aminotransferase, Amylase, Aspartate Aminotransferase, Urea Nitrogen, Calcium, Chloride, Creatinine Phosphokinase, Creatinine, Direct Bilirubin, y-Gamma-Glutamyl Transpeptidase, Glucose, High-Density Lipoprotein, Lactic Dehydrogenase, Lipase, Potassium, Sodium, Phosphorus, Total Bilirubin, Total Cholesterol, Triglyceride, Total Protein, Uric Acid, total carbon dioxide (TCO2), Anion Gap, antibody, protein, nucleic acid, molecules relative weight smaller than 1000 Dalton.

24. The method of claim 16, further comprising:
calculating a ratio between an intensity of the optical response at the wavelength of the optical response and an intensity of an optical response at a reference wavelength in the detected spectrum, and
determining the concentration of the at least one substance using the result of the calculation.

25. The method of claim 16, wherein the first agent is selected from the group consisting of ion-selective fluorescent reporter proteins and a protein that undergoes a change in fluorescence upon binding with an analyte.

26. The method of claim 16, further comprising mixing the magnetic bead in the fluid.

27. The method of claim 16, further comprising detecting, via the first optical detector, fluorescence or luminescence emitted by the first agent activatable from interaction with the at least one substance, and detecting, via the second optical detector, light scattering of the first magnetic bead in an evanescent field.

28. The method of claim 16, wherein the window is comprised of a material optically transparent to only a spectrum of blue light.

* * * * *